US005683455A

United States Patent [19]

Tilmans

[11] Patent Number: 5,683,455
[45] Date of Patent: Nov. 4, 1997

[54] TRAINING APPLIANCE FOR A MUSCLE

[76] Inventor: Maurice Hubertus Josephina Tilmans, Nassaustraat 77, NL-5911 BT Venlo, Netherlands

[21] Appl. No.: 661,709

[22] Filed: Jun. 11, 1996

Related U.S. Application Data

[63] Continuation of Ser. No. 30,484, filed as PCT/NL91/00188, Oct. 2, 1991, abandoned.

[30] Foreign Application Priority Data

Oct. 2, 1990 [EP] European Pat. Off. ............ 90202605.3

[51] Int. Cl.⁶ .................................................. A61F 1/10
[52] U.S. Cl. ............................................. 623/3; 600/16
[58] Field of Search ................................. 623/3; 600/16, 600/17, 18

[56] References Cited

U.S. PATENT DOCUMENTS 4,240,409 12/1980 Robinson et al. ...................... 623/3
4,530,496 7/1985 Smith et al. ........................... 272/68
4,919,661 4/1990 Gibney ................................... 623/6
4,979,936 12/1990 Stephenson et al. ................ 600/16

FOREIGN PATENT DOCUMENTS 0216042 4/1987 European Pat. Off. .

*Primary Examiner*—Randy C. Shay
*Attorney, Agent, or Firm*—Young & Thompson

[57] ABSTRACT

Implantable training appliance for a muscle, which is present for supporting the heart muscle, having a first chamber (3) which is filled with a gaseous and/or a liquid medium, has elastically deformable walls (4), and is surrounded by the muscle to be trained, and is connected to a second chamber (10, 11) which is connected to the first chamber and can exert a counterpressure on a medium flowing into the second chamber (10, 11). Through the periodic stimulation of the muscle surrounding the first chamber (3), to and fro flow of the medium between the two chambers is achieved by repeatedly compressing the first chamber (3). After sufficient muscle training the chambers are removed and the remaining hollow muscle is connected to the circulation system as a heart-supporting pump.

8 Claims, 2 Drawing Sheets

TRAINING APPLIANCE FOR A MUSCLE

This application is a continuation of application Ser. No. 08/030,484, filed as PCT/NL91/00188 Oct. 2, 1991, now abandoned.

FIELD OF THE INVENTION

The invention relates to a training appliance for a muscle to replace the heart muscle function for internal use.

THE KNOWN PRIOR ART

In "The Journal of Thoracic and Cardiovascular Surgery" 92; 733–746, 1986 "An autologous biologic pump motor" by Michael A. Acker et al. and in the same periodical 1987, 94; 163–174 "Skeletal muscle ventricles in circulation", also by Michael A. Acker et al., there are descriptions of a training appliance for a muscle which after a training programme has to take over at least a part of the heart function. In this case the training appliance comprises a hard core around which the muscle to be trained is wound. The muscle is activated by means of electrical pulses, in the course of which it proceeds to contract isometrically with a certain frequency around the hard core. Since a hard core is concerned in this case, the muscle is not trained in the optimum way. For this is only an imperfect simulation of the action which the muscle subsequently has to perform.

From U.S. Pat. No. 4,530,496 a training appliance for external use is known: This training device comprises a compressable chamber partially filled with a liquid. According to an embodiment of this U.S. patent specification a stem is connected to said chamber being provided with a scale. The quantity of liquid pumped in the stem by decreasing the volume of the chamber gives an indication of the force exerted on the chamber. This force can be read through the scale on the stem.

OBJECT OF THE INVENTION

The object of the invention is to provide a training appliance of the type mentioned above, in which the above-mentioned disadvantages are avoided which can be used for training of a muscle to replace the heart muscle function.

SUMMARY OF THE INVENTION

This object is achieved according to the invention in that training appliance comprises a first chamber to be filled with a fluid and provided with elastically deformable walls, while the chamber can be deformed between a first state in which the chamber takes up a maximum volume and a second state in which the chamber has a smaller volume than is the first state, and at least one second chamber in fluid connection with the first chamber, which second chamber has displaceable wall means for allowing increasing the volume of said second chamber and allowing the pressure in both of the chambers to equalize when the first chamber is in the second state.

These means preferably comprise an elastically deformable wall which in the first state of the first chamber defines a first volume and in the second state of the first chamber defines a second smaller volume.

In this way the counterpressure needed to train the muscle well can be generated very simply.

In another embodiment of the invention the means comprise a container which is separated by a deformable wall from the contents of the second chamber, which container is compressible. The container is preferably filled with a compressible medium such as gas.

This last embodiment is particularly advantageous if in this case the second chamber is formed completely inside the first chamber, and the second chamber is provided with a rigid wall which forms the division between the first and the second chamber.

In this way it is possible to obtain a training appliance which can be compressed by the muscle action, and in which sufficient counterpressure can be generated, but in which this compression causes no other external movements which could lead to possible irritation or pain in the area surrounding the implanted training appliance.

According to a further advantageous embodiment, the connection between the first and the second chamber has an increased resistance to flow of the fluid. In this way, during the training the resistance experienced during the pumping of liquid by a muscle, such as that experienced by a pumping heart muscle, can be simulated.

According to a further advantageous embodiment, the fluid introduced is a liquid. According to a further advantageous embodiment, one of the chambers is provided with introduction means for fluid. In other words, during the training of the muscle an increasing quantity of fluid, such as a liquid, can be introduced, so that the muscle can be subjected to an increasingly greater load, and in the process is increasingly further trained. In order to be able to observe the state of training of the muscle, according to the invention one of the chambers is provided with pressure observation means.

BRIEF DESCRIPTION OF THE DRAWINGS

Other features and advantages of the invention will become clear from the description which follows, with reference to the appended drawings, in which.

DETAILED DESCRIPTION OF THE INVENTION

Figure 1:
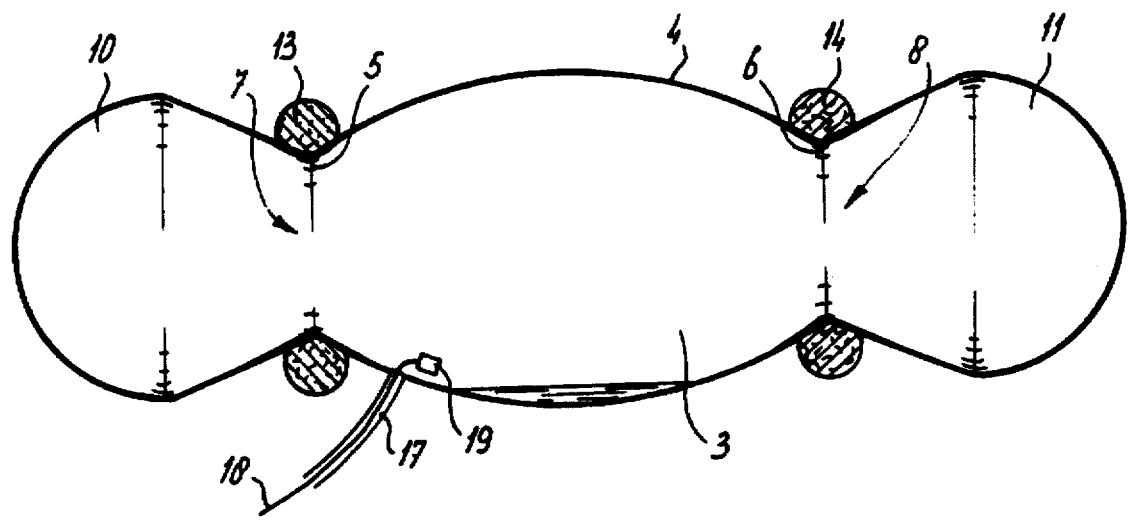
FIG. 1 is a schematic cross-section of a first embodiment of a training appliance according to the invention.

The training appliance, as shown in FIG. 1, comprises a first chamber 3, provided with an elastically deformable wall 4 made of an elastic plastic, such as silicone rubber of polyurethane. The chamber 3 is the shape of a wine cask with two end faces 5 and 6, where the first chamber 3 has a smaller cross-section. Near the end faces 5 and 6 the chamber 3 also has a greater wall thickness, in such a way that the resistance to deformation of the chamber 3 increases from the centre in the direction of the end faces 5 and 6. Apertures 7 and 8 are present in both end faces.

A second chamber 10, 11 is formed on each end face 5 and 6 respectively, preferably of the same material as the first chamber 3. In order to guarantee the shape of the assembly consisting of the chambers 3, 10 and 11, a ring 13, 14 of, for example, felt material can be fitted around the chambers at the level of the end faces 5 and 6, which ring serves to hold in place the transition points during the operation of the training appliance. The chambers 3, 10 and 11 are partially or completely filled with a fluid, such as water or another liquid which is tolerated by the human body, for example silicone oil. In the case of partial filling with a liquid, the remainder of the volume is filled with a gas which is compatible with human tissue, such as air, oxygen or helium.

The training appliance according to FIG. 1 functions as follows. When the chamber 3 is compressed, for example by the muscle to be trained, the fluid present therein is pressed away in the direction of the apertures 7 and 8. In the case of a partial gas filling, the gas will be compressed in the process. Through the increase in the internal pressure in the chambers 10 and 11, the wall of said chambers will at a certain moment expand until the pressure exerted by said walls and any gas pressure present are in equilibrium with the force exerted by the muscle. When the muscle ceases to work, the pressure thus built up will ensure that any fluid present flows back to the chamber 3, with a simultaneous return of the walls of the chambers 10 and 11 to the state of equilibrium shown in FIG. 1. Any compressed gas will in the process return to the equilibrium pressure. The training appliance is then ready for the next contraction of the muscle to be trained.

Reference number 17 indicates a connection tube which is in free communication with the chamber 3 and which can be connected by means of a valve to a source for fluid provided outside the body. During the training programme the quantity of liquid inside the chambers can be increased through this tube 17, so that the force to be applied with the muscle to be trained can be increased. This can, if necessary, also take place by increasing the pressure of the gas present inside the chambers. A line 18 of a pressure-measuring sensor 19 is present in tube 17. It is possible to connect tube 17 to the environment by means of a so-called ports catheter. Such a catheter is placed under the skin. Fluid can be introduced into tube 17 using a hypodermic needle. The risk of infections is reduced in this way. It is possible to connect tube 17 to chambers 10 or 11, instead of to chamber 3. It is also possible to provide pressure sensor 19 with a transmitter, so that line 18 can be replaced. Rings 13 and 14 can be loose, or can be fixed to the appliance according to the invention. They can also be used for stitching the muscle tissue to them. After the muscle has been trained, the vessel prostheses can then be fixed to such rings in a simple manner. For that purpose, the rings 13 and 14 can also be provided with further fixing means.

Figure 2:
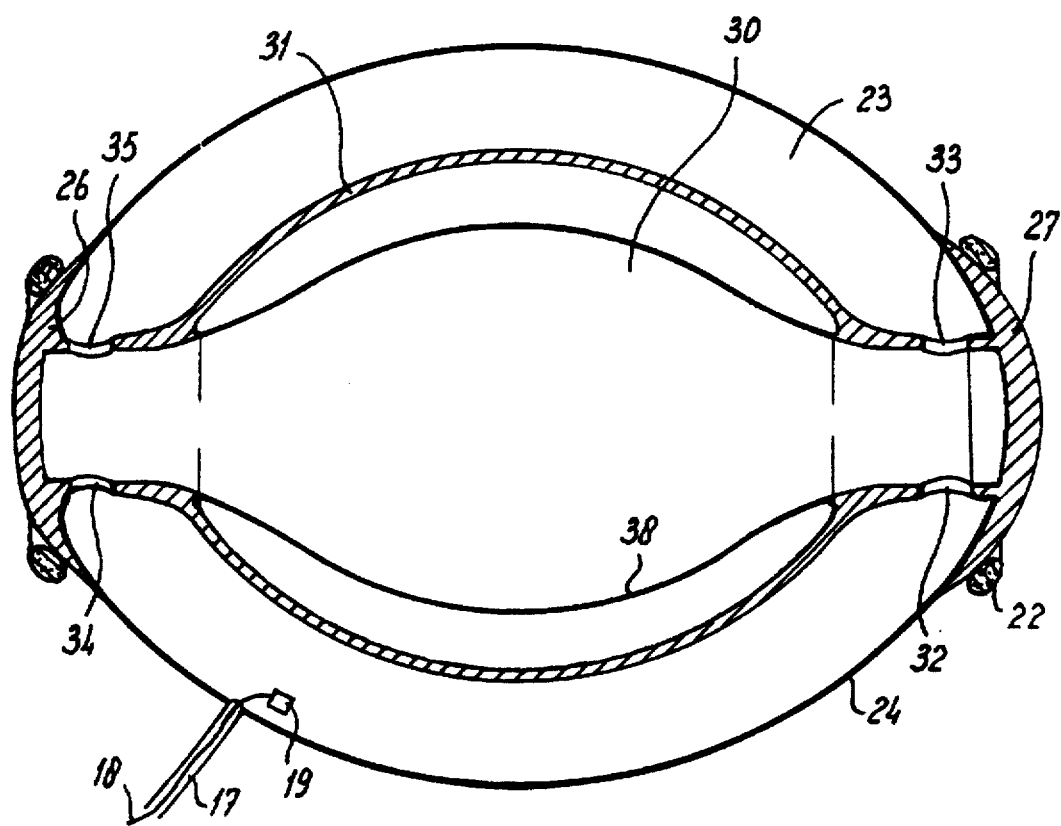
FIG. 2 is a schematic cross-section of a second embodiment of a training appliance according to the invention.

In the embodiment shown in FIG. 2, the training appliance comprises an oval chamber 23, with a wall 24. The wall 24 has near the short ends of the chamber 23 a thickened part 26 and 27 on which rings 22 are fitted. The end 27 in this case is in the form of a cover, by means of which the inside of the chamber 23 can be inspected if desired. The wall 24 is made of an elastically deformable plastic, such as silicone rubber.

Inside the chamber 23 a second chamber 30 is formed, having a rigid wall 31 which is provided essentially concentrically relative to the wall 24. The chambers 23 and 30 are in open communication with each other through apertures 32, 33, 34 and 35 provided near the ends 26 and 27, while the ends of the wall 31 are as it were in the form of cylindrical pipes connected to the parts 26 and 27, in which said apertures are provided. An elastically deformable gas-tight wall 38 is provided on the inside of the wall 31, this wall 38 compressing a displaceable wall means. The container space between walls 31 and 38 is completely filled with a gas under pressure. Both the chamber 30 and the chamber 23 are filled with a fluid, such as a liquid, possible a mixture of a gas and a liquid.

The way in which it works is essentially identical to that described with reference to FIG. 1. When the wall 24 is compressed, the fluid is pressed into the chamber 30 and will compress the gas there in the container between the walls 31 and 38 until a state of equilibrium has arisen. On stopping of the compression, the gas pressure will return the fluid, and consequently also the shape of the chambers, to the situation shown in FIG. 2. In the case of the embodiment shown here too, a tube 17 is present for the subsequent introduction of fluid, such as water, for increasing the efficiency of the muscle, and there is a pressure sensor 19 for observing the condition of the muscle.

Figure 3A:
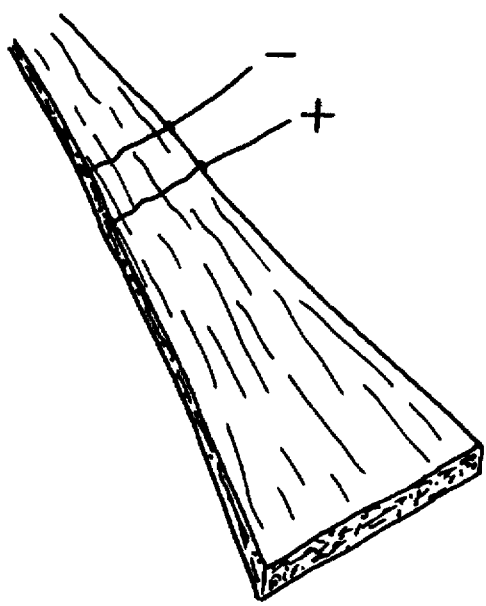
FIGS. 3a and 3d are a schematic representation of the different phases in the implantation of the training appliance in the human body.
Figure 3B:
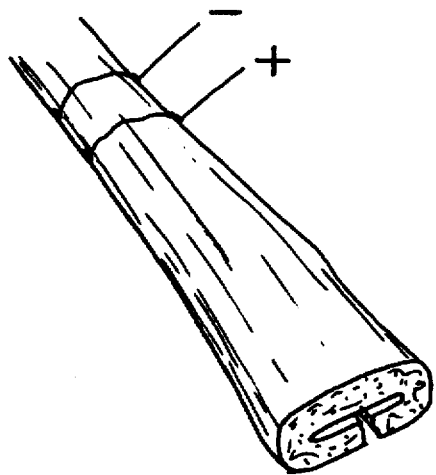
Figure 3C:
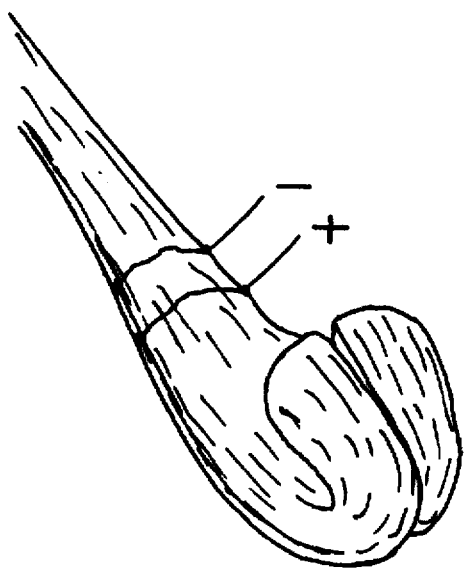
Figure 3D:
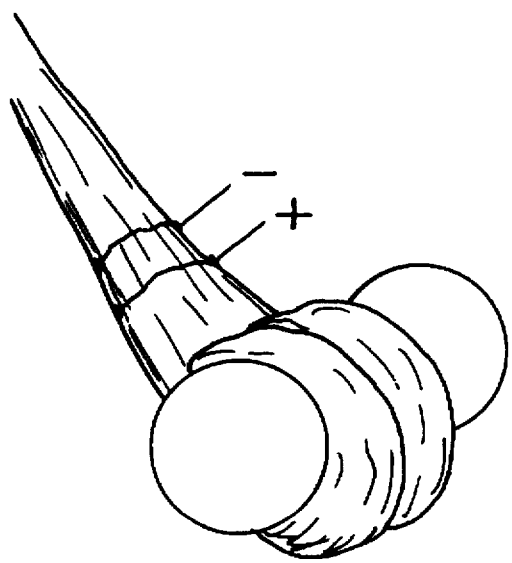

In order to use the training appliance for training a muscle to take over at least a part of the heart function, the procedure is as follows:

The implantation of the training appliance is shown schematically in FIGS. 3a, 3b and 3d. Use is made here of the usual techniques in heart operations.

After the patient has been put under an anaesthetic, the chest is opened in the vicinity of the heart. A skeletal muscle is then mobilised, which means that it is exposed at three sides, while one side remains connected to the body, along which side the connection to the nervous system and the blood vessels is maintained. Use is preferably made of the musculus latissimus dorsi, which—as shown in FIG. 3a—is mobilised until an essentially trapezoidal path is produced. Then, as shown in FIG. 3b, the longitudinal edges of the mobilised muscle are folded over towards each other, thus producing a sort of tube in which the nerves and the blood vessels can find a place. In the next phase the tube thus formed is rolled up from the free end, as shown schematically in FIG. 3c. Finally, the training appliance is also accommodated in the rolled-up muscle, as shown in FIG. 3d, the roll formed being fixed by known surgery techniques, for example by stitching.

Simultaneously with the mobilisation of the muscle, electrodes are coupled to the muscle, with the aid of which electrical signals can be supplied to the muscle, causing it to contract. The connection wires of said electrodes are further connected to a so-called myostimulator, by means of which the electrical pulses can be generated. During the closing of the body the myostimulator is fitted just under the skin. At the same time a connecting tube is fitted, at one side connected to the inside of the training appliance, and at the other side projecting outside, where it can be coupled to a source of the fluid to be used in the training appliance.

The training appliance is preferably positioned in such a way during closing of the wound that the rolled-up muscle part lies close to the heart and more or less takes up the position which it has to assume later when it has to take over part of the heart function. The myostimulator is then activated at a very low frequency, and the training process for the muscle begins. The object is to transform a fast muscle which is fatiguable and obtains its energy mainly from anaerobic processes to a slow muscle which is not fatiguable and takes its energy from aerobic processes. As is known, the heart muscle is an intermediate between these two types of muscles, and there is therefore the object of the training programme.

Immediately after the insertion of the device into the body, the training can start, as a result of which deterioration of the muscle tissue is avoided. In normal circumstances the training programme will take about six weeks, first the frequency and then the force to be generated gradually being increased through the introduction of more fluid, such as water, until the muscle is capable of working at a rhythm of, for example, 60 contractions per minute and a counterpressure of 130 mm Hg, circumstances which normally occur in a human body. This process can be followed if necessary by the pressure recorder, by which the necessary measurements can be carried out.

After reaching the desired state, the patient is operated on again, and the training appliance is removed. The muscle has acquired the shape of a hollow cylinder of which the interior space essentially corresponds to the periphery of the first chamber. Applying the usual heart surgery techniques, one opening at the end face of the muscle is connected by means of a non-return valve to the left atrium of the heart. The other opening is also connected by means of a non-return valve to the aorta, where the connection is preferably made to the aorta descendens. This is a desired application, but it is clear that other connections bridging the heart function can also be made. It is, however, known from experience that the pumping action of the left chamber is the first to begin to fail, since it has to generate the highest pressure. With the correct orientation of the non-return valves the muscle can now take over a part of the heart function, and blood is pumped directly from the left atrium to the aorta, and from there further into the body. Needless to say, the use of this method means that the need for spare hearts, which are permanently in short supply, can be reduced considerably, since the patient is capable himself of producing the necessary organs.

I claim:

1. Training appliance for a muscle to replace the heart muscle function for internal use, comprising a first chamber (3, 23) to be filled with a fluid and to be surrounded by said muscle said first chamber having elastically deformable outer walls (4, 24), while the first chamber (3) can be deformed between a first state in which the chamber takes up a maximum volume and a second state in which the chamber has a smaller volume than in the first state, and a second chamber (10, 11, 30) immediately adjacent to said first chamber and in fluid communication with the first chamber, said second chamber having displacable walls for allowing increasing the volume of the second chamber when the first chamber is in the second state, one of said first and second chambers having introduction means (17) for fluid, one of said chambers having pressure observation means (19).

2. Training appliance according to claim 1, in which said displaceable wall means comprise an elastically deformable wall (38) which in the first state of the first chamber bounds a first volume in the second state of the first chamber defines a second, larger volume of the second chamber.

3. Training appliance according to claim 1, further comprising a container space which is separated by a deformable wall from the content of the second chamber, which container space is compressible.

4. Training appliance according to claim 3, in which the second chamber (30) is formed completely inside the first chamber, and the second chamber is provided with a rigid wall (31) which forms the division between the first and the second chamber.

5. Training appliance according to claim 1, in which the second chamber (10, 11) is formed at one end of the first chamber.

6. Training appliance according to claim 1, in which the connection (13, 14) between the first and the second chamber comprises a fluid restriction.

7. Training appliance according to claim 1, in which the fluid is a liquid.

8. Training appliance for a muscle to replace the heart muscle function for internal use, comprising a first chamber (3, 23) to be filled with a fluid and to be surrounded by said muscle, said first chamber having elastically deformable outer walls (4, 24), while the first chamber (3) can be deformed between a first state in which the chamber takes up a maximum volume and a second state in which the chamber has a smaller volume than in the first state, said first chamber in said first state being barrel shaped, and two second chambers (10, 11, 30) immediately adjacent to and at opposite ends of said first chamber and in fluid communication with the first chamber, which second chambers having displaceable walls for allowing increasing the volume of said second chambers when the first chamber is in the second state, wherein one of said first and second chambers is provided with introduction means (17) for fluid.

* * * * *